United States Patent [19]
Thompson

[11] Patent Number: 5,731,509
[45] Date of Patent: Mar. 24, 1998

[54] ALMEN STRIP

[75] Inventor: Robert Alan Thompson, Quaker Street, N.Y.

[73] Assignee: General Electric Company, Schenectady, N.Y.

[21] Appl. No.: 674,953

[22] Filed: Jul. 3, 1996

[51] Int. Cl.⁶ .................. G01L 5/00; G01L 3/34
[52] U.S. Cl. .................................. 73/11.02; 73/12.09
[58] Field of Search ................. 73/11.01, 11.02, 73/11.03, 12.06, 12.09, 12.13

[56] References Cited

U.S. PATENT DOCUMENTS

| | | | |
|---|---|---|---|
| 3,638,464 | 2/1972 | Winter et al. | 72/53 |
| 3,695,091 | 10/1972 | Smith | 73/11.02 |
| 3,950,642 | 4/1976 | Feld | 73/762 |
| 4,470,292 | 9/1984 | DeClark | 73/11.02 |

*Primary Examiner*—Richard Chilcot
*Assistant Examiner*—Max H. Noori
*Attorney, Agent, or Firm*—Tyler Maddry; Donald S. Ingraham

[57] ABSTRACT

An almen strip has a plurality of corrugations on one surface while the opposite surface is smooth and flat. This strip measures directly peening intensity on chamfers.

13 Claims, 2 Drawing Sheets

ALMEN STRIP

BACKGROUND OF THE INVENTION

This invention relates to an almen strip. More particularly, this invention is directed to an improved almen strip for measuring peening intensity on chamfers.

Almen strips have been used for decades as the key element in shot peening process control. However, they are flat, and consequently valid only for peening on flat surfaces. Almen strips underestimate the intensity generated on chamfers where shot impact is more localized, and overestimate it in fillets where the impact is more conformal. When spherical shot strikes a flat surface a spherical cavity is produced. The material in the region of this dent is in a state of residual compressive stress because it was plastically stretched during impact. It is much more resistant to fatigue failure than untreated surface material because surface flaws are pressed together and their growth into cracks is inhibited. As the shot rains down, dents accumulate until the work surface is entirely covered with them and their associated compressive stress field. A convenient way of characterizing this process is with thin metal strips called almen strips.

Almen strips deflect in response to the surface compression produced by shot impacts. One impact will cause some deflection of the strip toward the side struck. As the impacts accumulate the deflection increases. Deflection is also greater if the impacts are more energetic, i.e., higher shot velocity and diameter. The almen strip is therefore a convenient way of assessing the overall peening process.

An almen strip is clamped in a special fixture and peened under a given set of conditions, such as, gun air pressure, shot size and shot mass flow rate. The deflections of many strips peened under these conditions and for varying amounts of time are then plotted on what is called a saturation curve. Saturation is said to occur when doubling the peening time has less than a 10% effect on deflection. For practical purposes, at saturation the strip is fully covered with impact dimples so its deflection is proportional only to the peening intensity, i.e. the depth of the surface compressive layer.

Coverage rate or the rate of approach to saturation depends on dimple size, the rate of dimple accumulation and statistics. Intensity or strip deflection at saturation is related to the energy of the impact, shot diameter, and the work material yield strength. Intensity is directly related to the size of a dimple, i.e., dimple diameter roughly equals compressive layer depth.

Typical almen strips are made from SAE 1070 cold rolled spring steel and have surface dimensions of 0.75"×3.00". Almen strips are commercially available in 3 thicknesses, 0.031" ("N"-strips), 0.051" ("A"-strips), and 0.093" ("C"-strips). The "A" strip enjoys the widest usage because its deflection roughly equals the depth of the surface compressive layer in the 0.004 to 0.010" range In other words a saturated strip which deflects 0.006" would have about a 0.006" thick compressive layer on the peened surface.

However, since they are flat, the intensity they measure is valid only for flat peened surfaces of similar dimensions. Therefore, a method is needed to determine intensity on critical surface features such as chamfers which are characterized by a high degree of curvature.

It is apparent from the above that there exists a need in the art for an improved almen strip to measure directly the peening intensity on chamfers. It is a purpose of this invention to fulfill this and other needs in the art in a manner more apparent to the skilled artisan given the following disclosure.

SUMMARY OF THE INVENTION

The above-mentioned needs are met by the present invention which relates to an improved almen strip. More particularly, the almen strip has a metal blank with opposite surfaces. One surface has a plurality of corrugations thereon. The other surface is smooth and flat. While the corrugations are normally longitudinal on the metal blank, vertical corrugations may be provided. The improved almen strip provides direct measurement of peening intensity on chamfers.

BRIEF DESCRIPTION OF THE DRAWINGS

The subject matter, which is regarded as the invention, is particularly pointed out and distinctly claimed in the concluding part of the specification. The invention, however may be best understood by reference to the following description taken in conjunction with the accompanying drawing figures in which:

DETAILED DESCRIPTION OF THE INVENTION

Figure 1:
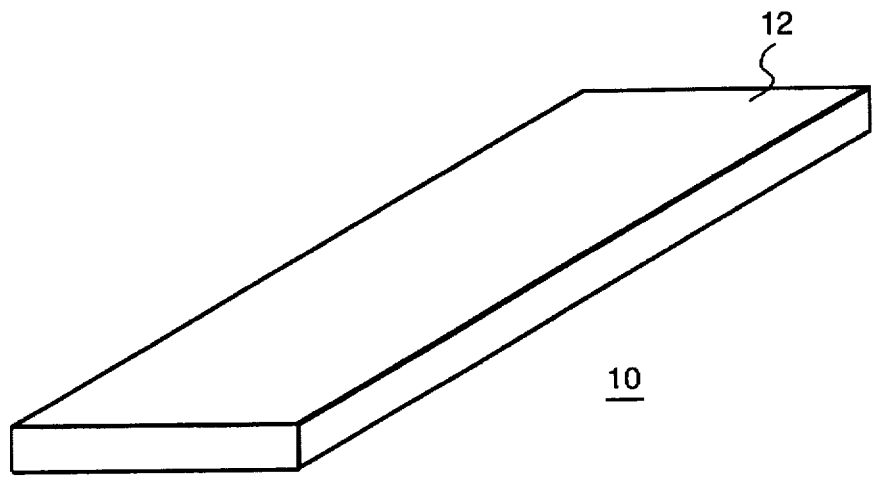
FIG. 1 is a schematic view of a conventional almen strip which is labeled as prior art.

FIG. 1 discloses a conventional almen strip 10 with a smooth, flat surface 12. This FIG. 1 has been labeled prior art. Almen strip 10 is made from SAE 1070 cold rolled spring steel with surface dimensions 0.75 inch width and 3.00 inches length. It is shown further as an "A" strip with a thickness of 0.051 inch. Such a strip measures intensity in a shot peening operation which is valid only for flat peened surfaces of similar dimensions.

Figure 2:
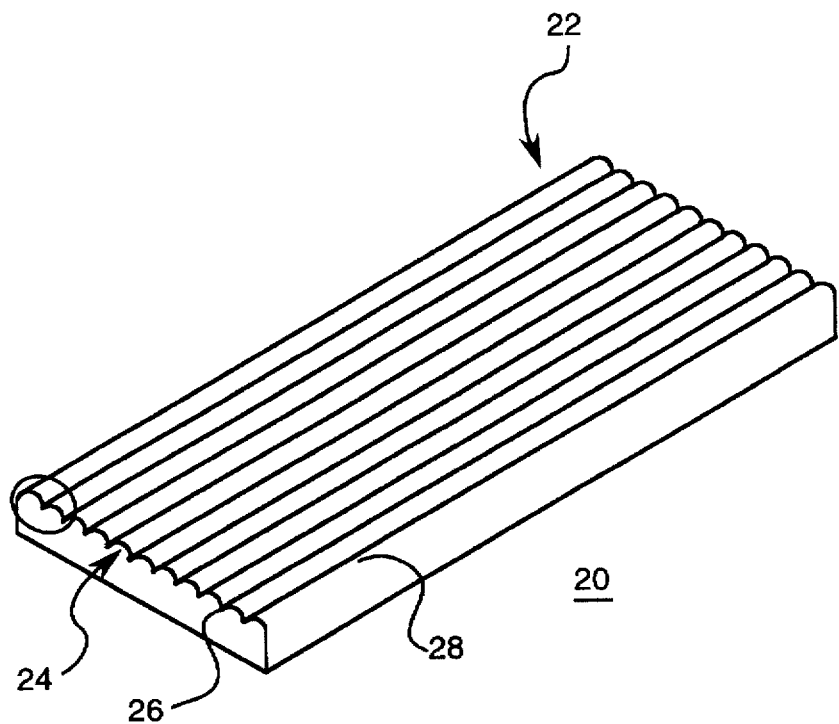
FIG. 2 is a schematic view of the improved almen strip of the present invention.

FIG. 2 discloses an improved almen strip 20 with a surface 22 having a plurality of longitudinal corrugations 24 with depressions 26 and peaks 28. Depressions 26 have widths of varying dimensions with the limitation that they are not wider than shot used in shot peening. In this manner, such shot cannot enter or become struck in the depressions 26 on the surface 22 of the almen strip 20. While it is not shown, such corrugations 24 may be provided in a vertical direction across the width of surface 22.

Almen strip 20 is made from SAE cold roller spring steel. The corrugations 24 on surface 22 are made by rolling them on flat strips of the steel as shown in FIG. 1.

The major dimensions of strips 20 are identical to strips 10 of FIG. 1, but the top surface is corrugated so that shot strikes on the surface correspond to those occurring when shot strikes a chamfered surface. At the same time, the bottom surface of the strip is flat. Furthermore, the thickness of the disclosed strip is adjusted so that it has the same bending moment of inertia as the conventional strip it models, be it an "A", "C", or "N"-strip. In this way, the strip can be used, and will give the same indication, as a conventional strip if its flat side is peened.

When a spherical ball strikes a flat surface such as an almen strip, it produces a shallow dent with a circular boundary. When, however, it strikes a highly curved surface such as a chamfer, the dimple boundary becomes elliptical and an ellipsoidal cavity is produced. For chamfers, since the area of contact between the ball and work surface is reduced, the ellipse has a smaller area than the circle, the dent is deeper, yielding a higher peening intensity.

This invention provides a convenient, verifiable means to capture this effect using the corrugated almen strip geometry. More specifically, the corrugated almen strip measures directly the shot peening intensity on chamfers. However, if the strip is peened on its corrugated side under identical peening conditions it will register a higher intensity due to the increased localization of the impacts.

The actual determination of the intensity of peening on a chamfer is determined in a fashion similar to conventional peening. That is, under given peening conditions corrugated strips are peened for varying times and a saturation curve is made like that described above for conventional strips. However, unlike flat strips, the resultant deflection doesn't represent the true intensity felt on the chamfer. This is because shadowing effects prevent the entire corrugated surface of the modified strip from being peened. To clarify this effect consider FIG. 3.

Figure 3:
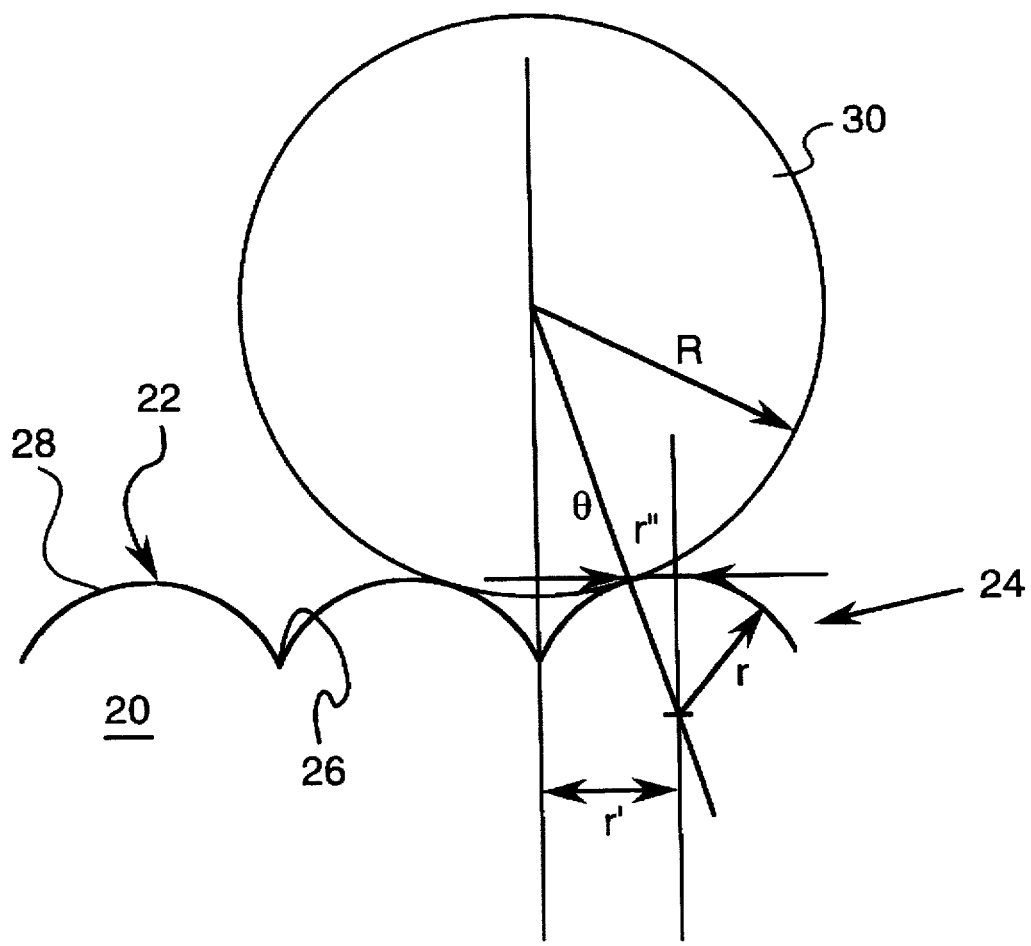
FIG. 3 is a schematic view of the kinematics of shot strike on the improved almen strip of FIG. 2.

FIG. 3 shows an end view of improved almen strip 20 of FIG. 2 with a surface 22 having a plurality of longitudinal corrugations 24 with depressions 26 and peaks 28. A ball 30 from a shot peening gun is shown striking strip 20. From the figure it is clear that the chamfer radius is about one half that of the shot, although the relative sizes of shot and chamfer do not effect the basic equation governing this behavior. It is clear that different combinations of the radii in FIG. 3 could be used to evaluate different size shot and chamfer radius combinations. This and other modifications which do not deviate from the basic intent of this disclosure will be obvious to the shot peening artisan and as such are considered a part of this invention. This figure shows the ball striking the midpoint between two peaks of the corrugated surface of the modified strip.

In the case illustrated the contact point is on the right hand corrugation. However a ball that strikes slightly to the left of this point will strike the adjacent corrugation.

As a consequence, only a certain portion of the corrugated strip gets peened. The valleys are shield assuring that the only impacts allowed are those representing peening on a chamfer of radius r with shot of radius R. The fraction of the surface which receives this peening is given as:

$$\% \text{ contact} = r''/r' = r/(r+R),\qquad(1)$$

where $$r'' = r \sin \theta;\qquad(2)$$

and where $$r' = (r+R) \sin \theta;\qquad(3)$$

Now, if the entire surface were peened at this intensity the deflection would increase. The increase would be in direct proportion to the increase in the peened portion. This effect can be represented mathematically as:

$$I\text{measured} = I\text{actual} \times \% \text{ contact}\qquad(4)$$

Since it is desired to know the actual intensity of the peening on the chamfer, i.e. Iactual, this equation must be inverted to give:

$$I\text{actual} = I\text{measured}/\% \text{ contact} = I\text{measured} \times (r+R)/r\qquad(5)$$

Therefore, if, for example, the shot and chamfer were of equal radius, the % contact would be $r/(r+R)=\frac{1}{2}$, and the true intensity of the peening would be two times that indicated by the strip deflection.

Although the strip shown in FIG. 2 has curvature in only one direction it can be used with good accuracy to measure most compound curvature effects such as those occurring on chamfered shafts, etc. This is because the shaft diameter is generally very large compared to that of the chamfer and is therefore for all practical purposes flat. The general law which governs this effect is $$R\text{effective} = (R\text{shaft} \times R\text{chamfer})/(R\text{shaft} + R\text{chamfer})\qquad(6)$$

On a ½" shaft with a 0.025" radius chamfer this equation gives an effective radius of $$R\text{effective} = (0.25 \times 0.025)/(0.25+0.025) = 0.023\qquad(7)$$

which is close to the actual chamfer radius. Only on very small diameter, chamfered parts would the compound curvature effect need to be considered.

The foregoing has described an improved almen strip to measure directly the peening intensity of chamfers. It will be apparent to those skilled in the art that various modifications thereto can be made without departing from the spirit and scope of the invention as defined in the appended claims.

What is claimed is:

1. An apparatus comprising:
    a metal almen strip with opposite surfaces;
    one surface with a plurality of corrugations thereon, wherein said metal almen strip almen strip registers a higher peening intensity due to increased localization of impacts on the corrugations and
    a second smooth and flat surface.

2. An apparatus as in claim 1, wherein the corrugations are in a longitudinal direction.

3. An apparatus as in claim 1, wherein the corrugations are in a vertical direction.

4. An apparatus as in claim 1, wherein said metal almen strip is cold rolled spring steel.

5. An apparatus as in claim 1, wherein the surface dimensions are 0.75 inch width and 3.00 inches length.

6. An apparatus as in claim 5, wherein the metal almen strip has a thickness such that a bending moment of inertia of the metal almen strip is substantially equal to a bending moment of inertia of an almen strip having two flat sides and a thickness of about 0.031 inch.

7. An apparatus as in claim 5, wherein the metal almen strip has a thickness such that a bending moment of inertia of the metal almen strip is substantially equal to a bending moment of inertia of an almen strip having two flat sides and a thickness of about 0.051 inch.

8. An apparatus as in claim 5, wherein the metal almen strip has a thickness such that a bending moment of inertia of the metal almen strip is substantially equal to a bending moment of inertia of an almen strip having two flat sides and a thickness of about 0.093 inch.

9. An apparatus comprising:
    a cold rolled spring steel almen strip with opposite surfaces;
    said almen strip having surface dimensions of 0.75 inch width and 3.00 inches length;
    one surface with a plurality of longitudinal corrugations thereon, wherein the said almen strip registers a higher peening intensity due to increased localization of impacts on the corrugations and
    a second smooth surface.

10. An apparatus comprising:
    an almen strip with a first surface and a second surface;
    wherein the first surface includes means for measuring a shot peening intensity on a peened surface which is not flat; and wherein the almen strip registers a higher peening intensity due to increased localization of impacts on said measuring means.

11. The apparatus of claim 10, wherein the means for measuring comprises a plurality of corrugations.

12. The apparatus of claim 11, wherein the corrugations include depressions which have a width which is less than or equal to a diameter of shot used in peening.

13. The apparatus of claim 10, wherein the almen strip has a thickness such that a bending moment of inertia of the almen strip is substantially equal to a bending moment of inertia of an almen strip having two flat sides and one of the following thicknesses: about 0.031 inches, about 0.051 inches and about 0.093 inches.

* * * * *